United States Patent [19]

Alisic et al.

[11] 4,161,676
[45] Jul. 17, 1979

[54] DEVICE FOR DISPLAYING VARIABLE QUANTITIES

[75] Inventors: Slobodan Alisic, Eindhoven; René H. Hamer, Rotterdam; Ludovicus A. H. Fleskens, St. Oedenrode, all of Netherlands

[73] Assignee: U.S. Philips Corporation, New York, N.Y.

[21] Appl. No.: 867,162

[22] Filed: Jan. 5, 1978

[30] Foreign Application Priority Data

Jan. 17, 1977 [NL] Netherlands ......................... 7700418

[51] Int. Cl.² .................... H01J 29/70; H01J 29/72
[52] U.S. Cl. .................... 315/395; 315/403; 315/388
[58] Field of Search ............... 315/389, 396, 397, 391, 315/403, 395, 388

[56] References Cited

U.S. PATENT DOCUMENTS 3,965,390  6/1976  Spencer, Jr. ......................... 315/397

Primary Examiner—Theodore M. Blum
Attorney, Agent, or Firm—Thomas A. Briody; Wiliam J. Streeter; Bernard Franzblau

[57] ABSTRACT

A device for displaying variable quantities on the viewing screen of a cathode-ray tube by means of deflection coils which are energized by a number of deflection amplifiers coupled to different supply voltages, the deflection amplifier with the lowest supply voltage serving for signal components with the lowest frequencies and that with the highest supply voltage for the signal components with the highest frequencies. This results in a substantial reduction in power consumption.

5 Claims, 5 Drawing Figures

DEVICE FOR DISPLAYING VARIABLE QUANTITIES

The invention relates to a device for displaying variable quantities, in particular physiological quantities, on a display screen of a cathode-ray tube, comprising a deflection unit with deflection coils for deflecting an electron beam produced in the cathode-ray tube, and at least one deflection amplifier, having an input adapted to receive a voltage which corresponds to the quantity to be displayed and having an output connected to a set of deflection coils.

Such devices are for example used for displaying the EEG, the ECG or the blood-pressure curve of a patient. The frequency spectrum of these quantities generally lies between 0 and a few hundred Hertz. For a correct reproduction of these signals on the display screen (stationary image) each signal must be displayed approx. 50 times per second. For this purpose a deflection amplifier having a bandwidth of approx. 100 kHz is required. The deflection amplifier is inductively loaded by the deflection coils, which means that for a specific variation in the deflection current the amplifier should supply a voltage which increases according as said variation is faster. The voltage which the amplifier can supply is determined by the supply voltage, which also determines the power consumption of the amplifier. As in known devices the supply voltage is selected so that the anticipated maximum frequencies are still correctly reproduced, the supply voltage is in fact too high for the lower frequencies so that more power is consumed than is necessary. Obviously this is a disadvantage, in particular when the device is battery-powered, which is frequently the case with devices for displaying physiological quantities.

It is an object of the invention to provide a device of the type mentioned in the preamble whose power consumption is substantially lower than that of known devices.

For this purpose the device in accordance with the invention is characterized in that at least two deflection amplifiers are provided which are powered with supply voltages of different magnitude, each of the deflection amplifiers with a supply voltage other than the highest supply voltage being connected to the set of deflection coils via a coupling element which is adapted to transfer signals from said deflection amplifier in the direction of the deflection coils substantially without distortion and substantially block signals in the opposite direction, the deflection amplifier with the highest supply voltage being destined for signal components with the highest frequencies and that with the lowest supply voltage for signal components with the lowest frequencies.

Preferably the inputs of all deflection amplifiers are connected to each other so as to form a common input.

The invention will be described in more detail with reference to the drawing in which.

Figure 1:
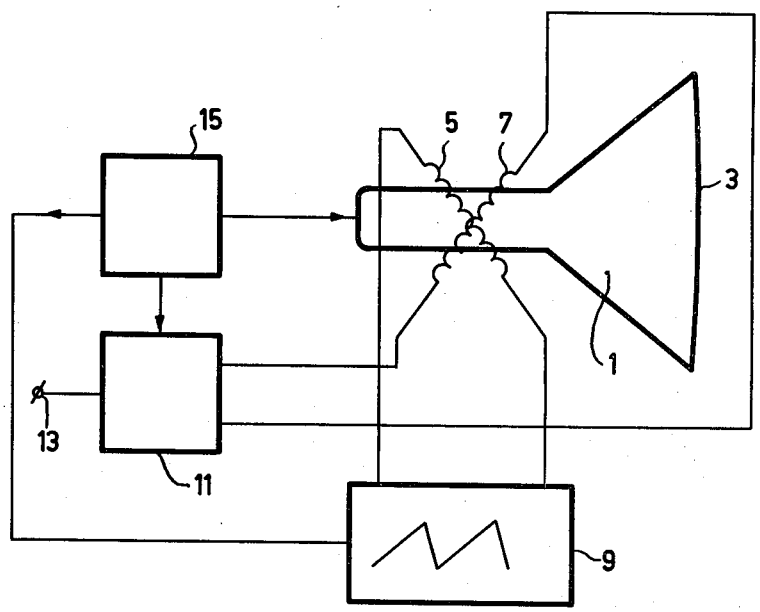
FIG. 1 is a block diagram of a device in accordance with the invention.

The device which is schematically shown in FIG. 1 comprises a cathode-ray tube 1 with a display screen 3 which is adapted to display variable quantities. A deflection unit consisting of two sets of deflection coils 5 and 7 is adapted to deflect an electron beam produced in the cathode ray tube 1 in a horizontal and a vertical direction respectively. Each set of deflection coils in known manner consists of at least two toroidal or saddle-shaped coils. The horizontal deflection coils 5 are energized with a sawtooth-shaped current by a time base generator 9. The vertical deflection coils 7 are energized with a current which corresponds to the quantities to be displayed by a deflection circuit 11 (a few examples of which are shown in FIGS. 2 through 5). For this purpose a voltage corresponding to said quantities can be applied to an input 13. A power supply unit 15 provides the various supply voltages for the cathode-ray tube 1, the time base generator 9 and the deflection unit 11. The power supply unit 15 itself may be operated from the A.C. supply or it may be battery-powered.

Figure 2:
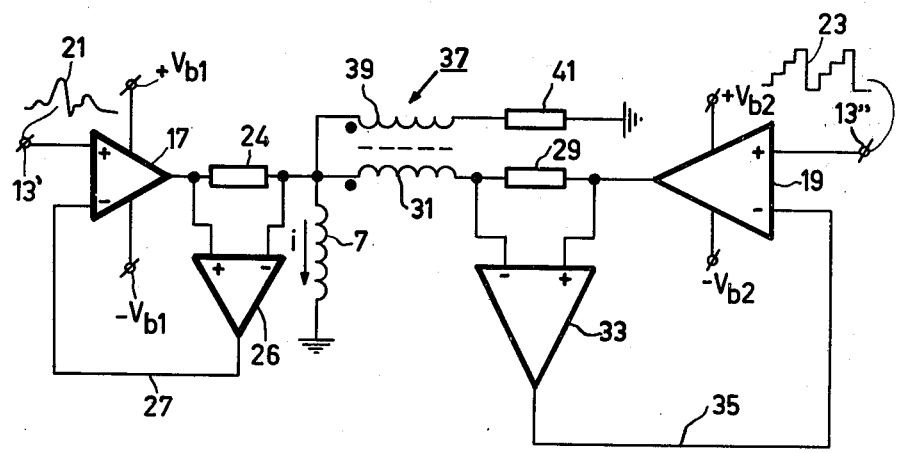
FIGS. 2 through 5 show diagrams of various examples of deflection circuits to be used in the device of FIG. 1.

FIG. 2 shows a diagram of a first example of the deflection unit 11. This unit comprises two deflection amplifiers 17 and 19 which receive different supply voltages $V_{b1}$, $V_{b2}$ from the power supply unit 15 (see FIG. 1). The first deflection amplifier 17 is supplied with the higher supply voltage $V_{b1}$ and is destined for rapidly varying quantities, for example an ECG signal 21, which is applied to an input 13'. The second deflection amplifier 19 is supplied with the lower supply voltage $V_{b2}$ and is destined for slowly varying quantities, for example a staircase positioning signal 23 which is applied to an input 13''. The positioning signal is a direct voltage which increases in steps and serves to enable different physiological signals to be displayed one above the other. If for example in addition to the ECG signal 21 a number of further quantities are to be displayed, one of these signals is applied to the input 13' during the time that the positioning signal 23 has a specific value. When the positioning signal assumes a higher value, the next signal is applied to the input 13'. The value of the positioning signal 23 is then each time added to the value of the signal corresponding to the quantity to be displayed so that the various quantities are displayed on the display screen 3 one above the other.

The output of the first deflection amplifier 17 is connected to the deflection coils 7 via a resistor 24 across which a voltage appears which is proportional to the deflection current. This voltage is fed back to the (−) input of the deflection amplifier 17 (current feedback) via an amplifier 26 and a conductor 27.

The output of the second deflection amplifier 19 is also connected to the deflection coils 7 via a resistor 29 and a coil 31. Via an amplifier 33 and a conductor 35 the resistor 29 also provides feedback of a voltage which is proportional to the output current of the amplifier 19. The coil 31 is the secondary winding of a transformer 37, whose primary 39 is grounded via a resistor 41. This transformer functions as a coupling element which transfers the signals from the second deflection amplifier 19 to the deflection coils 7 substantially without distortion and which substantially blocks the signals from the first deflection amplifier 17 to the resistor 29. For this purpose the output voltage of the first deflection amplifier 17 is applied to the primary 39 of the transformer 37. The coupling factor and the winding directions of the windings have been selected so that the primary 39 induces a voltage into the secondary winding 31 which is equal and opposite to the voltage produced across the deflection coil 7 by the deflection amplifier 17. As a consequence the total voltage across the feedback resistor 29 only depends on the output voltage of the second deflection amplifier 19.

The deflection amplifier 19 is inductively loaded at its output by a series connection of the coils 31 and 7. If L is the inductance of this series connection, a voltage $V = L(di/dt)$ is required for a specific variation of the deflection current i through the deflection coil 7. From this it follows that for rapid variations of the current i a high supply voltage $V_b$ is required because the output voltage V of the amplifier is obviously never higher than the supply voltage $V_b$. The signal 23 is a signal which always remains constant for some time and which can thus be displayed with a comparatively low supply voltage $V_{b2}$. However, this means that changes in the level of the signal 23 are followed by the deflection current i with a slight delay only, but generally this will present no problem. The advantage of the low supply voltage is that the power consumed by the deflection amplifier 19, which equals $V_{b2} \cdot i$ is also low. Conversely, a higher supply voltage $V_{b1}$ is needed for the deflection amplifier 17 for faithfully reproducing rapid variations in the ECG signal 21. However, this signal also contains low-frequency components for which the supply voltage and thus the power is in fact too high.

A further improvement can be obtained by a circuit arrangement in which all low-frequency components of both signals 21 and 23 are amplified by the deflection amplifier 19 supplied with the lower supply voltage $V_{b2}$ and in which the deflection amplifier 17 supplied with the higher supply voltage $V_{b1}$ only functions as a correction amplifier which adds the high-frequency components to the deflection current i. Such a circuit arrangement is shown in FIG. 3.

The upper part of this Figure is identical to that of FIG. 2, but the (+) inputs of the deflection amplifiers 17 and 19 are now interconnected via a variable resistor 43 so as to form a common input 14. In this case current feedback of the amplifier 17 is obtained via a resistor 25 which is connected in series with the deflection coils 7. The (+) input of the deflection amplifier 19 is furthermore connected to a resistor 45, whose other end is connected to ground. The common input 14 is connected to the output of a summation device 47 which in the present example has two inputs 13' and 13" to which voltages 21 and 23 can be applied. These voltages are added in the summing device 47 and the sum signal appears at the common input 14. The deflection amplifier 19, as is described hereinbefore, will then produce a deflection current $i_2$ in the deflection coils 7, which is as far as possible proportional to the sum signal. However, owing to the comparatively low supply voltage $V_{b2}$ the high-frequency components of the sum signal are not represented in the deflection current $i_2$ or only in attenuated form. Owing to its higher supply voltage $V_{b1}$ the deflection amplifier 17 will now be capable of producing a deflection current $i_1$ which adds said missing high-frequency components. The total deflection current $i = i_1 + i_2$ is then a faithful representation of the signal at the common input 14. The circuit functions in an optimum manner when the variable resistor 43 is adjusted so that, viewed from the common input 14, the sensitivities of the two deflection amplifiers 17 and 19 are equal to each other.

Figure 3:
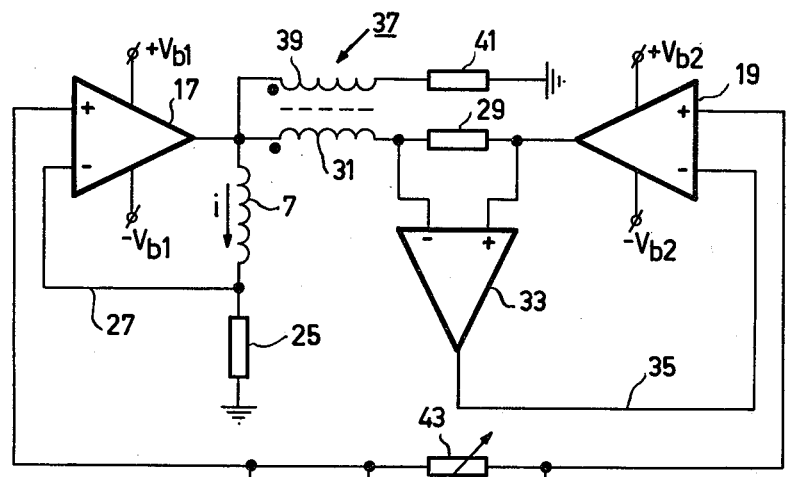
Figure 4:
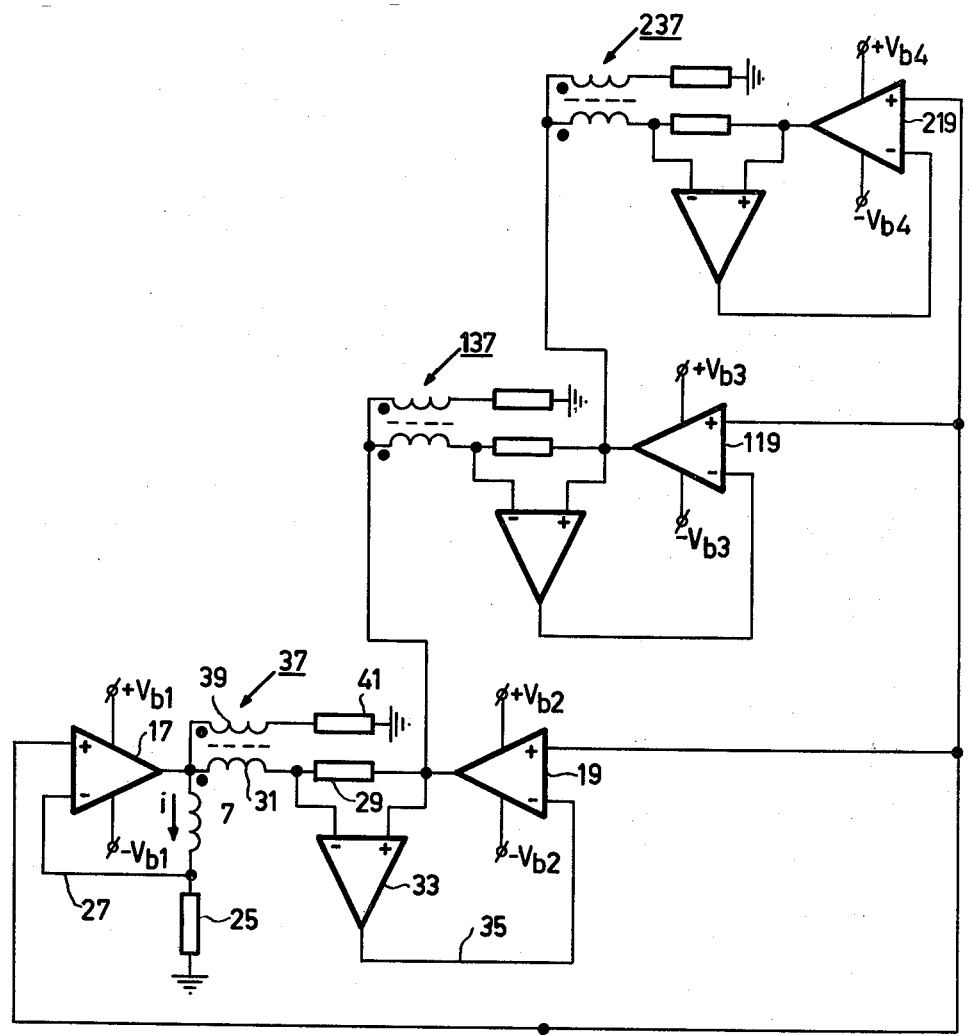

In the circuit arrangement of FIG. 3 the sum signal is separated into two groups of components, namely components with low and components with high frequencies. A further sophistication is possible by dividing the signal into more groups of components, wherein for each group a deflection amplifier is provided whose supply voltage is adapted to the frequencies of said group. An example of this embodiment is shown in FIG. 4. In addition to the deflection amplifiers 17 and 19 with supply voltages $V_{b1}$ and $V_{b2}$ mentioned in the previous example, two further deflection amplifiers 119 and 219 with supply voltages $V_{b3}$ and $V_{b4}$ are provided. These voltages are arranged such that $V_{b1} > V_{b2} > V_{b3} > V_{b4}$. The output of the fourth deflection amplifier 219 is connected to the output of the third deflection amplifier 119 via a transformer 237 whose function is the same as that of the transformer 37. The third deflection amplifier 119 in its turn is connected to the output of the second deflection amplifier 19 via a similar transformer 137. All the deflection amplifiers have a common input 14 which may be connected to a summing device as is shown in FIG. 3. Each deflection amplifier receives information about the total contribution to the deflection current which is delivered by all the deflection amplifiers with a lower supply voltage and by itself. As an example, the sum of the deflection currents supplied by the deflection amplifiers 219, 119 and 19 flows through the resistor 29 and the voltage across this resistor is fed back to the (−) input of the deflection amplifier 19. As is apparent from the Figure, the same applies for the other deflection amplifiers. Owing to the choice of the supply voltages the fourth deflection amplifier 219 will produce a deflection current $i_4$ which represents the components with the lowest frequencies in the signal applied to the common input 14, whereas the third deflection amplifier 119 produces a deflection current $i_3$ which represents the components with slightly higher frequencies, and the second amplifier 19 a deflection current $i_2$ which represents the components with still slightly higher frequencies. Finally the first deflection amplifier 17 supplies a deflection current $i_1$ which represents the components with the highest frequencies. The total deflection current $i = i_1 + i_2 + i_3 + i_4$ is then a faithful representation of the signal at the common input 14 and for each group of components only the minimum required power is used. Obviously, the number of deflection amplifiers need not be limited to four. The optimum number inter alia depends on the frequency spectrum of the signals applied to the input 14. If desired, the sensitivities of the various deflection amplifiers can be rendered variable in a similar way to that effected with the variable resistor 43 in the example of FIG. 3.

Figure 5:
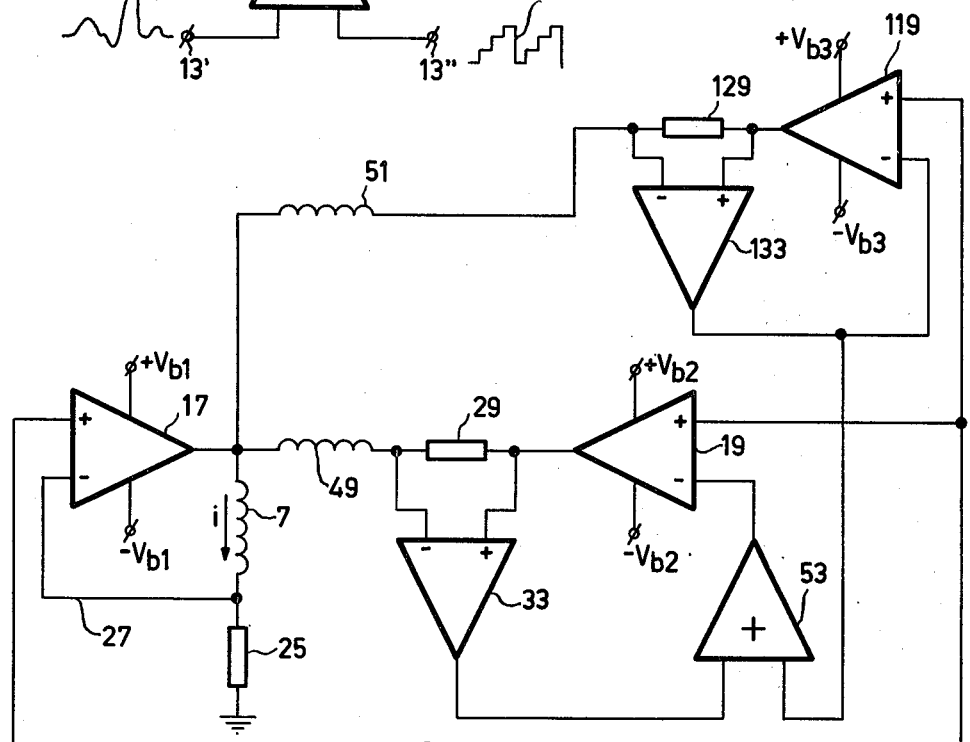

FIG. 5 shows an example in which the transformers have been replaced by chokes. In this example there are three deflection amplifiers 17, 19 and 119 with a common input 14. For the supply voltages the following relation is valid again: $V_{b1} > V_{b2} > V_{b3}$. The output of the second deflection amplifier 19 is connected to the deflection coils 7 via a first choke 49 and the output of the third deflection amplifier 119 is connected to the deflection coils via a second choke 51. The inductance of said chokes must be so high that the following requirements are met:

$$V_{b1} \cdot \frac{Z_{19}}{Z_{19} + X_{49}} < V_{b2}$$

and $$V_{b1} \cdot \frac{Z_{119}}{Z_{119} + X_{51}} < V_{b3}$$

Here $Z_{19}$ is the output impedance of the deflection amplifier 19, $X_{49}$ the impedance of the choke 49, $Z_{119}$ the output impedance of the deflection amplifier 119, $X_{51}$ the impedance of the choke 51, all values at the lowest frequency $f_0$ to be processed by the first deflection amplifier 17. If these requirements are met the output signal of the first deflection amplifier is not fed back to the feedback resistors 29 and 129 of the deflection amplifiers 19 and 119.

The circuit furthermore includes a summing amplifier 53, whose two inputs are connected to the outputs of the feedback amplifiers 33 and 133, which provide the current feedback for the deflection amplifiers 19 and 119. The output of this summing amplifier is connected to the (−) input of the deflection amplifier 19 so that this deflection amplifier receives information about the contributions to the deflection current i by the third deflection amplifier 119 as well as the second deflection amplifier 19, in a similar way as in the case described in the example of FIG. 4.

What is claimed is:

1. A device for displaying variable quantities on a display screen of a cathode ray tube comprising, a deflection unit including deflection coils for deflecting an electron beam produced in the cathode ray tube and at least two deflection amplifiers, at least one deflection amplifier having an input adapted to receive a signal voltage which corresponds to the quantity to be displayed and an output connected to a set of deflection coils, power supply means including a plurality of terminals for supplying operating voltages ranging from a highest supply voltage value to a lowest supply voltage value, means coupling at least two of said deflection amplifiers to respective voltage supply terminals of the power supply means so that said deflection amplifiers are powered with supply voltages of different magnitude, means connecting each of the deflection amplifiers which are coupled to a supply voltage other than the highest supply voltage to the deflection coils via a coupling element which is adapted to transfer signals from the deflection amplifier in the direction of the deflection coils substantially without distortion and to substantially block signals in the opposite direction, the deflection amplifier with the highest supply voltage being adapted to amplify signal components with the highest frequencies and the deflection amplifier with the lowest supply voltage being adapted to amplify signal components with the lowest frequencies.

2. A device as claimed in claim 1 wherein the inputs for all deflection amplifiers are connected together so as to form a common input.

3. A device as claimed in claim 2 further comprising a summing device having an output connected to the common input of all of the deflection amplifiers and a plurality of inputs adapted to receive respectively a plurality of signal voltages corresponding to the quantities to be displayed.

4. A device as claimed in claim 1 wherein the coupling element comprises a transformer with a primary winding and a secondary winding, a first end of the secondary winding being connected to the output of a deflection amplifier that is coupled to a supply voltage terminal other than the highest supply voltage, and the other end of said secondary winding being connected to the output of a deflection amplifier that is coupled to a higher supply voltage terminal and to one end of the primary winding to form a common junction point, the other end of said primary winding being connected to a point of fixed potential via an impedance element, the coupling factor and the winding direction of the two transformer windings being selected so that a voltage is induced in the secondary winding which is equal and opposite to the voltage between the common junction point of the two windings and a terminal of the deflection coils which is not connected to the outputs of the deflection amplifiers.

5. A device as claimed in claim 1 wherein the coupling element comprises a choke having one end connected to the output of a deflection amplifier that is coupled to a supply voltage terminal other than the highest supply voltage and another end connected to the output of the deflection amplifier coupled to the highest supply voltage terminal and to the deflection coils, the choke inductance being selected so that:

$$V_{b1} \cdot Z/(Z+X) < V_{b2},$$

where
- $V_{b1}$ = the supply voltage of the last-mentioned deflection amplifier,
- $V_{b2}$ = the supply voltage of the first-mentioned deflection amplifier,
- $Z$ = the output impedance of the first-mentioned deflection amplifier at a frequency $f_0$,
- $X$ = the impedance of the choke at the frequency $f_0$, and
- $f_0$ = the lowest frequency to be processed by the last-mentioned amplifier.

* * * * *